United States Patent [19]
Hakky et al.

[11] Patent Number: 6,023,639
[45] Date of Patent: Feb. 8, 2000

[54] NON-INVASIVE BODILY FLUID WITHDRAWAL AND MONITORING SYSTEM

[76] Inventors: Said Hakky, 8547 Merrimoor Blvd. East, Largo, Fla. 33777-3145; A-Hamid Hakki, 1508 Sturbridge Ct., Dunedin, Fla. 34698

[21] Appl. No.: 09/071,343

[22] Filed: May 1, 1998

[51] Int. Cl.[7] .................................................. A61N 1/30
[52] U.S. Cl. .............................. 604/20; 604/22; 604/289; 604/313; 128/635
[58] Field of Search ................................ 604/20, 22, 289, 604/290, 306, 310, 312, 313; 600/309, 365, 573, 578, 579; 607/2, 75; 424/448, 449

[56] References Cited

U.S. PATENT DOCUMENTS

| | | | |
|---|---|---|---|
| 4,786,277 | 11/1988 | Powers et al. | 604/20 |
| 5,291,887 | 3/1994 | Stanley et al. | 604/289 |
| 5,458,140 | 10/1995 | Eppstein et al. | 600/573 |
| 5,617,851 | 4/1997 | Lipkovker | 600/573 |
| 5,733,255 | 3/1998 | Dihn et al. | 604/20 |
| 5,746,711 | 5/1998 | Sibalis et al. | 604/20 |
| 5,771,890 | 6/1998 | Tamada | 604/20 |
| 5,810,806 | 9/1998 | Ritchart et al. | 606/45 |
| 5,879,323 | 3/1999 | Henley | 604/20 |
| 5,885,211 | 3/1999 | Eppstein et al. | 600/573 |

*Primary Examiner*—Ronald K. Stright, Jr.
*Assistant Examiner*—David J. Cho
*Attorney, Agent, or Firm*—Rosenberg, Klein & Lee

[57] ABSTRACT

A system for non-invasively withdrawing and monitoring bodily fluids from the skin of a user is provided. The system apparatus includes a portable hand-held housing (16) having an internal chamber (9). Fluid displacement mechanism (1) is removably coupled to the housing (16) for directing the fluid from the skin into the internal chamber (9). The fluid displacement mechanism (1) has a first end (20) adapted to be located on an outer surface of the skin and an opposing second end (21) located internal the housing (16). Vacuum pump (10) in the housing (16) non-invasively extracts the fluid from the skin and draws the extracted fluid into the internal chamber (9) through the fluid displacement mechanism (1). A monitoring mechanism within the internal chamber (9) monitors the fluid drawn into the chamber (9).

10 Claims, 8 Drawing Sheets

NON-INVASIVE BODILY FLUID WITHDRAWAL AND MONITORING SYSTEM

BACKGROUND OF THE INVENTION

1. Field of the Invention

The subject invention relates to the withdrawal and monitoring of fluids from the body of a patient or user. More particularly, the subject invention is directed to a portable system for non-invasively withdrawing bodily fluids from the skin of a patient or user. Further, the subject invention is directed to the monitoring of the fluid non-invasively withdrawn from the skin. Even further, the subject invention directs itself to sensing a constituent in the extracted fluid and to the analysis of said constituent to determine a quantitative characteristic thereof.

The subject invention is further directed to the non-invasive withdrawal of a bodily fluid from the skin of a user or a patient by applying to the user's skin a predetermined combination of negative pressure and ultrasonic energy. Even further, the subject invention is directed to the non-invasive withdrawal and monitoring of bodily fluid from the skin of a user by applying to the user's skin a predetermined combination of negative pressure and an electric field, where the electric field applied to said skin induces electrical currents on the skin. Alternatively, the non-invasive withdrawal of bodily fluid from the skin is further effected by applying a predetermined combination of negative pressure, ultrasonic energy, and an electric field to the skin of the user.

2. Prior Art

Prior art non-invasive techniques for delivering substances to a patient's skin include sonophoresis (application of ultrasound energy to the skin to enhance substance delivery to the skin) and iontophoresis (the application of electric fields to the skin to induce currents therein to facilitate substance delivery to the skin). Also known in the prior art is the technique of sonophoretic extraction of bodily fluids from the skin, as is described in U.S. Pat. No. 5,617,851, by Lipkovker.

In addition to these prior art systems, other relevant prior art is directed to apparatuses and methods for monitoring substances or constituents of interest present in bodily fluids, including the determination of glucose concentrations in such bodily fluids.

However, the prior art fails to teach or suggest a system for non-invasively withdrawing or extracting fluid from the skin of a patient or user in accordance with the teachings of the subject invention. It follows that the prior art fails to teach or suggest a system that provides the particular methodology of the subject invention for both non-invasively withdrawing and monitoring fluids from the skin of a user.

SUMMARY OF THE INVENTION

It is an object of the subject invention to provide a non-invasive system for withdrawing and monitoring fluids from a user's or a patient's skin. The apparatus provided to perform these functions includes a portable, hand-held housing having an internal vacuum chamber. Removably coupled to an open end of the housing is a fluid displacement mechanism which displaces or directs fluid from the user's skin toward and then into the internal vacuum chamber. The fluid displacement mechanism has a first end positionally located contiguous an outer surface of the skin from where the bodily fluid is to be non-invasively extracted, and an opposing second end disposed internal the apparatus housing.

Mounted to, or within the apparatus housing is an operable mechanism for non-invasively extracting the bodily fluids from the skin of the user or patient, whereby the non-invasively extracted fluid is drawn into the internal vacuum chamber through the fluid displacement mechanism. In addition to these components, a monitoring circuit including a sensing transducer is positioned within the internal chamber of the apparatus housing for monitoring the fluid drawn into the internal chamber.

In a first embodiment of the subject invention, the mechanism for non-invasively extracting the fluid from the skin includes a vacuum generator in open communication with the internal chamber for generating a negative pressure of a predetermined magnitude therein, and an ultrasonic transducer that is coupled to the internal chamber for generating ultrasonic energy, which negative pressure and ultrasonic energy are transmitted through the fluid displacement mechanism for combined application to the user's skin.

In a second embodiment of the subject invention, the non-invasive mechanism for extracting fluid from the skin includes the vacuum generator for generating the negative pressure, in combination with an electric field generator, coupled to the housing, that is in tactile communication with the skin for inducing a current therein.

In a third embodiment, the non-invasive mechanism for extracting the bodily fluid includes a predetermined combination of negative pressure, generated by the vacuum generator, ultrasonic energy, generated by the ultrasonic transducer, and an electric field, generated by the electric field generator, all of which are applied to the skin of the user to facilitate extraction of bodily fluids therefrom.

DESCRIPTION OF THE PREFERRED EMBODIMENTS

The subject invention relies on the ability of skin to secrete bodily fluids. The histological foundation for this ability lies with the structure or composition of skin. Histologically, the skin can be regarded as being composed of two layers, the superficial and relatively avascular epidermis, and the deeper vascular dermis. The epidermis, having few blood vessels and nerves, is composed of the stratum cornium, stratum lucidum, stratum granulosum, stratum spinosum, and stratum basal. The stratum cornium is the most superficial layer and varies in thickness from 2–3 cell layers to many layers in the sole of the feet. The cells of the stratum cornium essentially contain no nucleii. In fact, the protoplasm in these cells has been transformed into a horny material or keratin. The cells of the stratum lucidum are flattened, closely packed cells with flattened nucleii. The stratum granulosum consists of 2–3 layers of spindle-shaped cells with the stratum spinosum consisting of polyhedral cells.

Lymphatic fluid, or extracellular fluid, circulates between the epidermis cells. This fluid is essentially in equilibrium with the cells of the epidermis. The extracellular and the intracellular fluid of the epidermis forms the basis of the subject invention for measuring blood glucose or other blood constituents without the use of a needle: that is, the non-invasive withdrawal and monitoring of fluids from a user's skin.

In general, the lymphatic fluid in the epidermis is kept inside of the body by the presence of the stratum cornium, and by the wall of the blood vessels in this vicinity. In certain areas of the skin, the stratum cornium is merely 2 or 3 cells in thickness. Thus, if negative pressure (a vacuum or suction) is applied to these thin areas of the skin, fluid sampling or withdrawal from the skin can be achieved without the use of a needle, as glucose and other electrolyte ions having a low molecular weight diffuse through the skin responsive to the negative pressure applied thereto.

The fluid sample first withdrawn under negative pressure from the skin is a characteristically clear fluid, such clear fluid being representative of a fluid sample from the extra-cellular as well as the intracellular fluid from the superficial cells of the epidermis. The concentration of glucose or other electrolytes present in this fluid is representative of the status of the glucose or other electrolytes found in the circulating blood below the skin.

If the vacuum pressure applied to the skin becomes more negative, i.e., more suction is applied to the skin, then the fluid sample extracted from the epidermis will be transformed from the initially clear fluid to a bloody fluid, as small blood capillaries with weak walls in the epidermis are ruptured under the increased vacuum pressure applied to the skin.

The apparatus and methods of the subject invention take advantage of negative pressure to non-invasively withdraw fluids from the skin of a user, however, the subject invention advantageously combines the affect of negative pressure with other processes that further facilitate non-invasive fluid withdrawal. For instance, in a first embodiment of the subject invention, a gentle vacuum suction or predetermined negative pressure is applied to the epidermis in combination with sonophoresis (the application of ultrasound energy to the epidermis). This combination further facilitates the sampling or speedy withdrawal from the skin of the human glucose, electrolytes, peptides, hormones, or steroids without the use of a needle, and with no adverse side effects to the patient. Essentially, low frequency ultrasound waves (10–90 kHz) disrupt the cohesiveness of the superficial cell layers of the skin thus softening the keratin layer of the stratum cornium. This process of sonophoresis realigns and softens the superficial cellular cement (stratum cornium) thus creating gaps in the superficial layers of the epidermis. Such disruptive action, coupled with the presence of the negative pressure, facilitates the speedy extraction of bodily fluid from the intracellular or extracellular fluid of the epidermis.

Once the bodily fluid has been withdrawn in accordance with the above-mentioned non-invasive withdrawal technique, a variety of monitoring techniques well known in the prior art can be applied to the extracted fluid to determine various quantitative (or qualitative) characteristics of the constituents of the fluid. For instance, several techniques may be employed to determine the concentration of glucose present in the extracted fluid. One such technique, optical rotation sensing, exploits the fact that the glucose molecule, when present in the extracted fluid, introduces a dextrorotation to light incident thereto, the extent of rotation varying in proportion to the concentration of the glucose in a given extracted fluid sample. Thus, a monitoring device which measures the optical rotation, experienced by light projected through the extracted and collected fluid, can determine the concentration of the glucose therein. Similarly, steroid or peptide molecules introduce a levo-rotation to light incident thereto which can be exploited to determine the presence and concentration of such constituents in the withdrawn bodily fluid.

With regard to the measurement of glucose concentration, an even more accurate determination of concentration can be made with a monitoring device that exploits a quantitative chemical reaction between the glucose in the extracted fluid and an enzyme, glucose oxidase, added thereto. In this reaction, the amount of enzyme that reacts with the glucose is in proportion to the concentration of the glucose in the bodily fluid. Thus, once this amount has been determined, the concentration of glucose can be readily measured. To determine the amount of the enzyme that has reacted with the glucose, a color reagent is added to the enzyme such that when the enzyme is added to the extracted bodily fluid (which includes glucose) for reaction therewith, the resulting color of the fluid represents the amount of the enzyme that has reacted with the glucose, which, as stated above, reflects the concentration of glucose in the extracted fluid. Sensing the color of the fluid provides an accurate measure of the concentration of glucose.

U.S. Pat. No. 5,617,851, by Lipkovker, U.S. Pat. No. 4,366,033, by Richter et al, and U.S. Pat. No. 4,440,175, by Wilkens, are representative of well known prior art methods and apparatus used to determine the concentration of a substance such as glucose, in a bodily fluid.

In a second embodiment of the subject invention, a gentle vacuum suction or predetermined negative pressure is applied to the epidermis in combination with an electric field. This application of an electric field to the skin and the corresponding inducement of currents therein to facilitate the migration of bodily fluid through the skin, has been termed "ionotophoresis" in the prior art. The combination of negative pressure and iontophoresis further facilitates the sampling or speedy withdrawal from the skin of the bodily fluids containing the various constituents of interest therein. As in the first embodiment of the subject invention, this non-invasive withdrawal of bodily fluids is achieved without the use of a needle, and with no adverse side effects to the patient.

As will be described later, in this second embodiment, an electric field is applied to the skin through a pair of oppositely charged, spaced-apart tactile electrodes that are in physical contact with the skin. This application of an electric field to the skin induces small currents (on the order of microamperes) therein as ionic molecules carried in the fluids of the skin migrate through the skin under the influence of the electric field applied thereto. Such ionic movement in the superficial layers of the epidermis disrupts the cohesiveness of the superficial cell layers. This disruption, coupled with the application of negative pressure to the skin, accelerates the extraction of bodily fluids from the cellular as well as the extracellular fluid of the epidermis. The non-invasively extracted fluids are subsequently monitored for constituents of interest.

The third embodiment of the subject invention, in essence, combines the processes developed in the previous two embodiments to non-invasively withdraw and monitor fluids from the skin. In particular, a gentle vacuum suction or predetermined negative pressure is applied to the epidermis in combination with both sonophoresis and iontophoresis, in the manner described in relation to the first and second embodiments of the subject invention. This combination of effects produced by the negative pressure, iontophoresis (described previously) and sonophoresis (described previously) facilitates the speedy withdrawal of bodily fluid from the skin without any adverse side effects to the patient. The fluid thus extracted is monitored for constituents of interest, as in the first and second embodiments of the subject invention.

As previously described, the first embodiment of the subject invention is directed to a non-invasive system and method for withdrawing and monitoring fluids from a user's skin by applying a predetermined combined negative pressure (vacuum suction) and ultrasonic energy to the skin. Referring to FIGS. 1–6, the portable apparatus used to non-invasively withdraw bodily fluids from the user's skin comprises a hand-held unit or housing 16 removably coupled to a disposable fluid displacement means 1. Housing 16 includes handle grip portion 7 at an outer surface of housing 16, a vacuum cylinder or internal chamber 9 within housing 16, and a plurality of operable component members disposed within, or being mounted to, housing 16.

Figure 1:
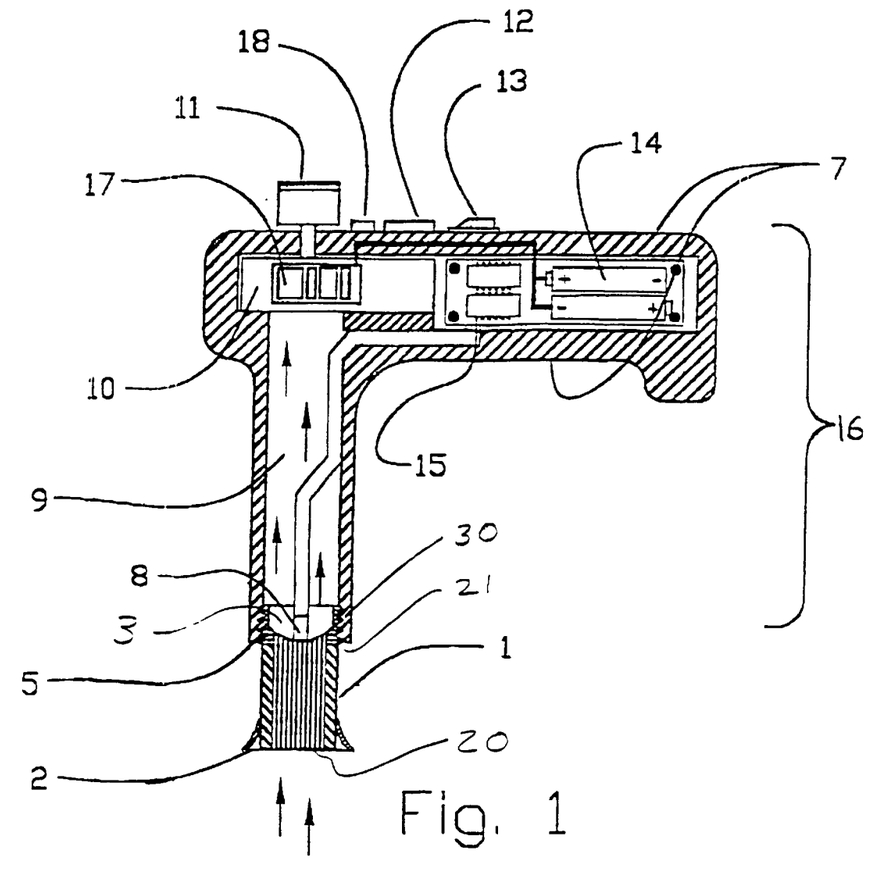
FIG. 1 is an elevational cross-sectional view of the first embodiment of the apparatus of the subject invention.

Vacuum pump 10 is mounted internal housing 16 in open fluid communication with internal chamber 9 for generating a vacuum suction or negative pressure thereby driving the bodily fluids from fluid displacement mechanism 1 upwardly into chamber 9. Vacuum gauge 11 is coupled to vacuum pump 10 for providing an indication of the negative pressure induced by vacuum pump 10 within internal chamber 9 providing the operator with an indication of the pressure drop during operation. Vacuum control unit or adjustment mechanism 13 permits the operator or user of the apparatus to adjust to a predetermined level the negative pressure generated by vacuum pump 10 within internal chamber 9. Vacuum control unit 13 may be operated by any well known electronic control such as a potentiometer. Piezo-metal ultrasound or ultrasonic transducer 17 generates ultrasound energy which is directed toward fluid displacement mechanism 1. Electronic sensing transducer 8 is disposed in proximity to fluid displacement mechanism 1, and has a transducer output electrically coupled to logic chips or analysis mechanism 15. Display mechanism 12, which may be a standard LCD display, is electrically coupled to an output of analysis mechanism 15 for displaying various results therefrom. Electrical power source or batteries 14 are mounted in a forward compartment of housing 16 for providing electrical energy to electrically powered vacuum pump 10, ultrasound transducer 17, logic chips 15 and display 12. Electrical switch 18 selectively activates and deactivates the vacuum pump 10 and ultrasonic transducer 17.

Fluid displacement mechanism 1 is formed essentially as a tubular structure (see FIGS. 2–4) having a plurality of capillary conduits, or micro-tubules, formed therein extending between a first end 20 and a second opposing end 21 of fluid displacement mechanism 1. Sealing member 2 is mounted about the peripheral edge of first end 20, whereas screw threads 5 are provided at second end 21. Sealing member 2 may be in the form of a vacuum cup having resilient sidewalls for flexibly engaging and suctionally gripping the skin. Screw threads 5 threadingly engage corresponding threads provided at an open end 30 of housing 16. Thus, fluid displacement mechanism 1 is removably coupled to housing 16, at open end 30, through screw threads 5. Clearly, any coupling mechanism known in the prior art can be substituted for the screw threads 5 so long as a relatively air-tight seal is formed at the coupling interface between housing 16 (at open end 30) and second end 21 of fluid displacement mechanism 1. For instance, press-fit engagement mechanism, flange-type engagement mechanism, or any other engagement mechanism which provides this relatively air-tight interface coupling would suffice.

First end 20 of fluid displacement mechanism 1 is adapted to be pressed into contiguously interfacing and sealing engagement with that area of the user's skin from which bodily fluids are to be non-invasively extracted. Sealing member 2 mounted about the periphery of first end 20 of fluid displacement mechanism 1 is thus adapted to provide a substantially air-tight seal between itself and the user's skin contacting the seal. This sealing interface need only be sufficiently air-tight to ensure that vacuum pump 10 can generate a negative pressure within internal chamber 9, which negative pressure is communicated through the plurality of capillary conduits 4 for application to the skin of the user contiguously interfacing first end 20 of fluid displacement mechanism 1. In this configuration, air is drawn through the plurality of capillary conduits 4, and along internal chamber 9 toward vacuum pump 10 (as shown by the arrows in FIG. 1).

Since, the negative pressure required to extract fluid from the epidermis varies with the thickness of the stratum cornium (the thicker the stratum cornium, the more negative pressure is required to extract fluid from these superficial layers of the epidermis), advantageously, the negative pressure generated by vacuum pump 10 within internal chamber 9 is displayed to an operator on the vacuum gauge 11. Thus, a predetermined desired negative pressure can be achieved by tuning vacuum adjustment control 13 so that vacuum gauge 11 reads this predetermined negative pressure value.

Figure 2:
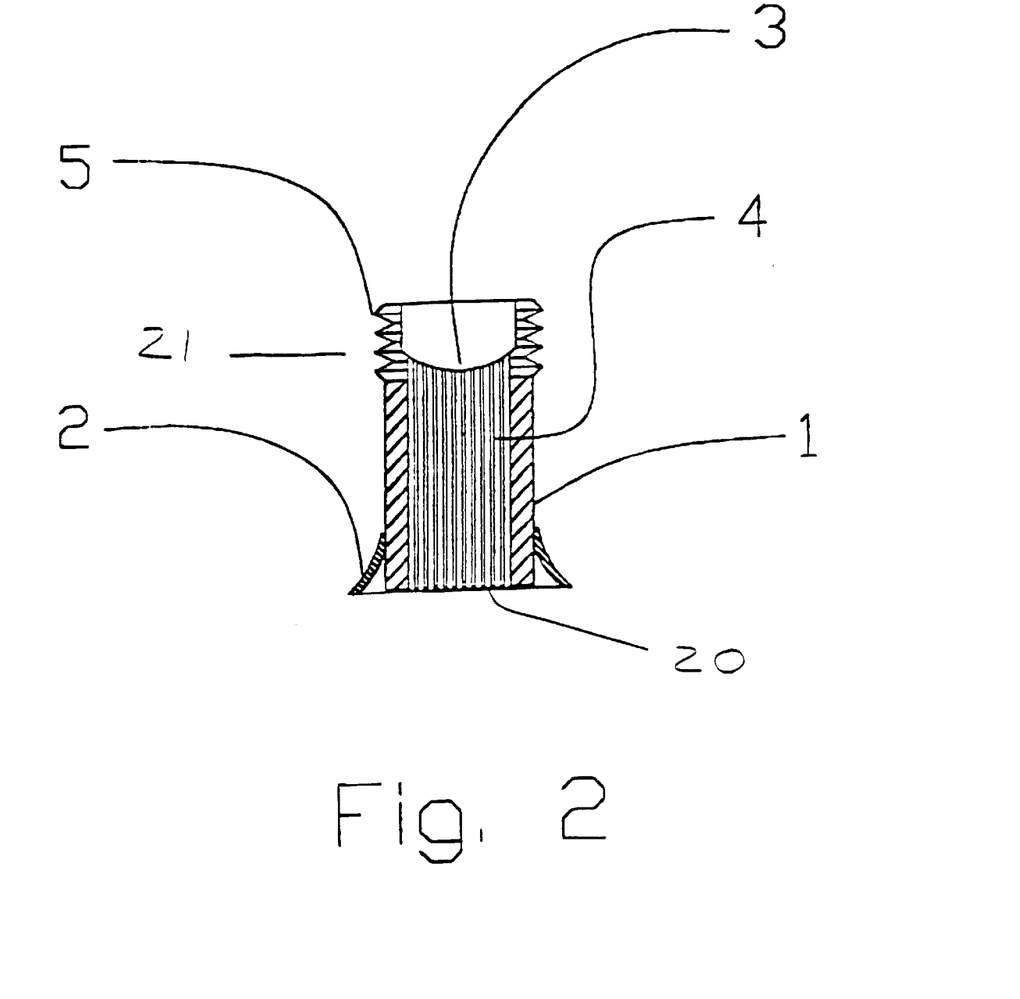
FIG. 2 is an elevational cross-sectional view of the fluid displacement mechanism shown in FIG. 1.
Figure 3:
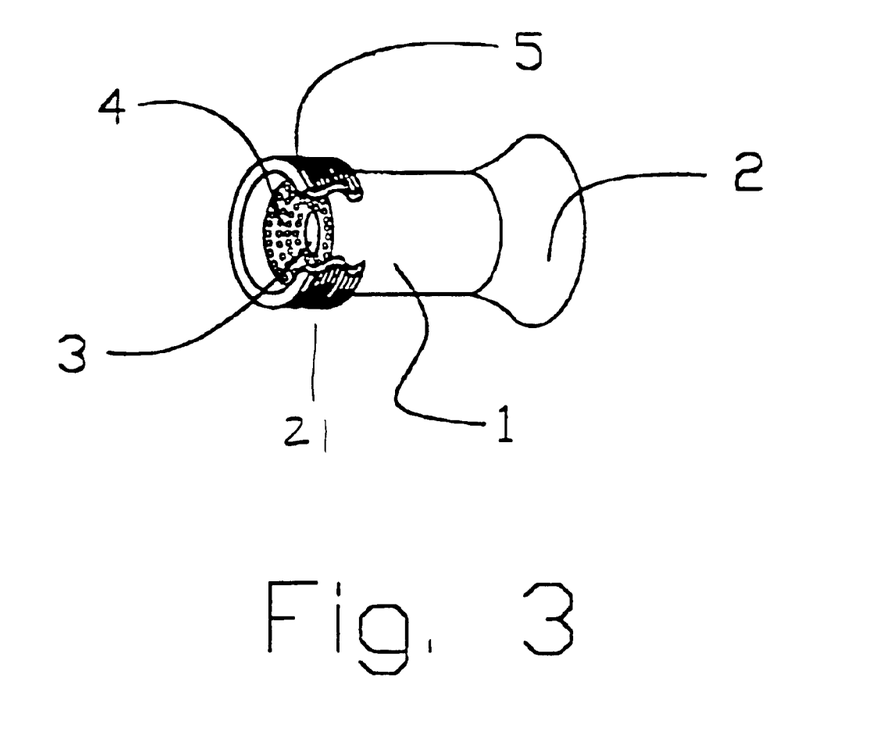
FIG. 3 is a perspective view of the fluid displacement mechansim shown in FIG. 1.
Figure 4:
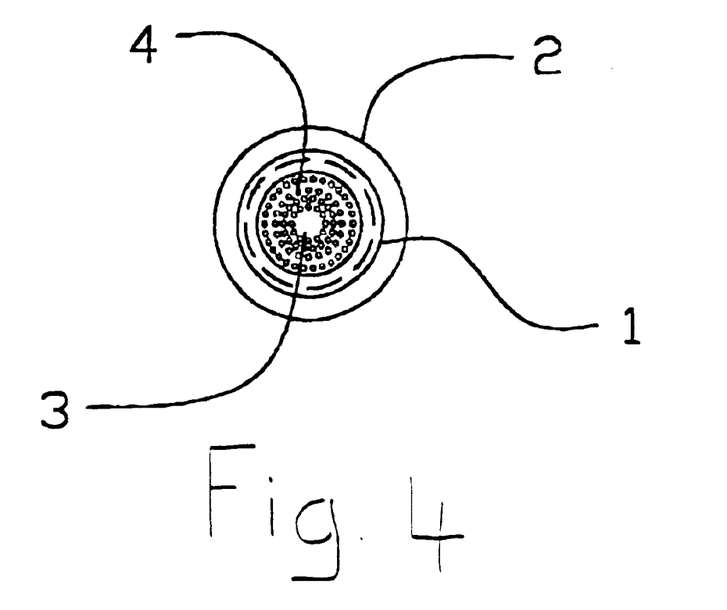
FIG. 4 is a frontal view of the fluid displacement mechanism.

Fluid displacement mechanism 1 further includes a fluid collecting reservoir or trough 3 disposed within the tubular structure at second end 21 (see FIGS. 2–4). Any fluid non-invasively extracted from the skin contiguously interfacing first end 20 of fluid displacing mechanism 1, is drawn through the plurality of capillary conduits 4 toward second end 21 whereat the plurality of capillary conduits empty their fluidic contents into this collecting reservoir 3.

As shown in FIG. 1, when fluid displacement mechanism 1 is appropriately coupled to open end 30 of housing 16, electronic sensing transducer 8 is positioned so as to be in close proximity with fluid collecting reservoir 3. With this arrangement, sensing transducer 8 is maintained at all times in fluid communication with bodily fluids that are non-invasively extracted from the skin of the user, contiguously interfacing first end 20 of displacement mechanism 1, and that have traversed capillary conduits 4 to be emptied into fluid collecting reservoir 3. Thus, any bodily fluids non-invasively withdrawn through the skin of the user which are displaced along capillary conduits 4, and into the fluid collecting reservoir 3, are sensed by electronic sensing transducer 8 disposed within the fluid collecting reservoir 3.

The method of operation used to non-invasively withdraw and monitor fluids using this first embodiment begins with the action of attaching fluid displacement mechanism 1 to housing 16 using screw threads 5. The proper coupling of fluid displacement mechanism 1 to housing 16 brings electronic sensing mechanism 8 into fluid communication with fluid collecting reservoir 3 disposed within internal chamber 9. Switch 18 is positioned to energize both vacuum pump 10 and ultrasonic transducer 17. The switch 18 enables batteries 14 to power both of these devices. With both vacuum pump 10 and ultrasonic transducer 17 energized, the apparatus is ready for deployment to the user's skin from where bodily fluids are to be extracted. The user or other operator grasps handle grip 7 of housing 6 and then applies the lower end 20 of fluid displacing mechanism 1 to the selected area of the user's skin.

Both the negative pressure generated by vacuum pump 10 within internal chamber 9 and the ultrasonic energy generated by ultrasonic transducer 17 are directed through fluid displacement mechanism 1 and the capillary conduits 4 therewithin, to the user's skin contiguously interfacing first end 20 of fluid displacement mechanism 1. The combination of negative pressure and ultrasonic energy applied to the skin of the user ensures a speedy extraction of bodily fluid from the intracellular and/or extracellular fluid of the epidermis contiguously interfacing first end 20 of fluid displacement mechanism 1, which non-invasively extracted bodily fluid is directed by the plurality of capillary conduits 4 into fluid collecting reservoir 3 for contact with electronic sensing transducer 8.

Ultrasound transducer 17 is generally adapted to generate ultrasound waves having a frequency range extending between 10 and 90 kHz. However, ultrasound waves can be generated at any frequency outside this range, as long as the ultrasound waves produce a sonophoretic affect that enhances fluid withdrawal from the skin.

Once the desired amount of extracted fluid has been emptied into fluid collecting reservoir 3, for example 1–10 microliters, an accurate quantitative measurement can be made of a constituent of the extracted fluid. For instance, if a determination of glucose concentration within the extracted fluid is required, using the enzyme glucose oxidase test described previously, then sensing transducer 8 operates as a color sensing transducer generating an electrical output responsive to the color of the collected fluid (which color is responsive to the enzyme glucose oxidase test). The electrical signals generated by sensing transducer 8 are electrically coupled from an output thereof to the logic chips 15 located on logic motherboard 40, mounted within housing 16 (see FIGS. 1 and 5).

Figure 5:
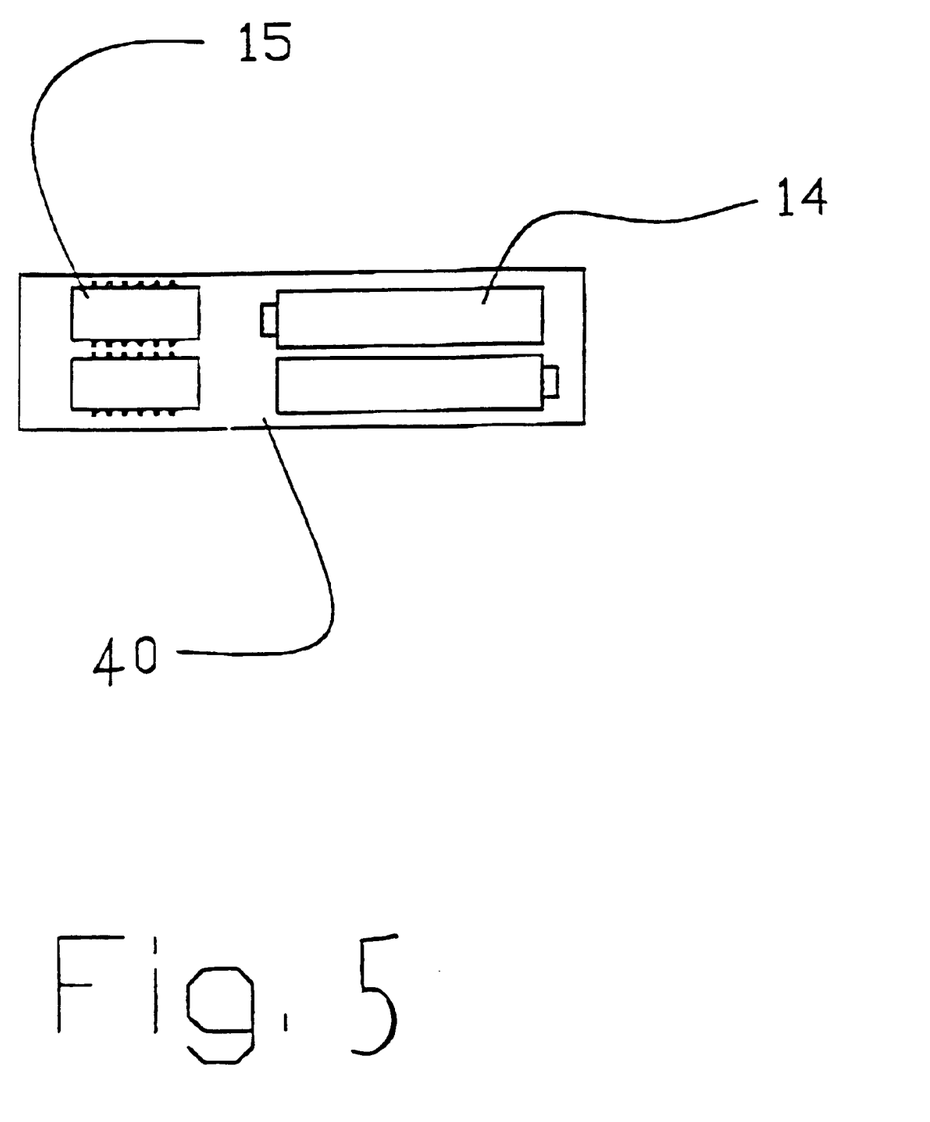
FIG. 5 is a top view of a logic board and electronic components thereon.
Figure 6:
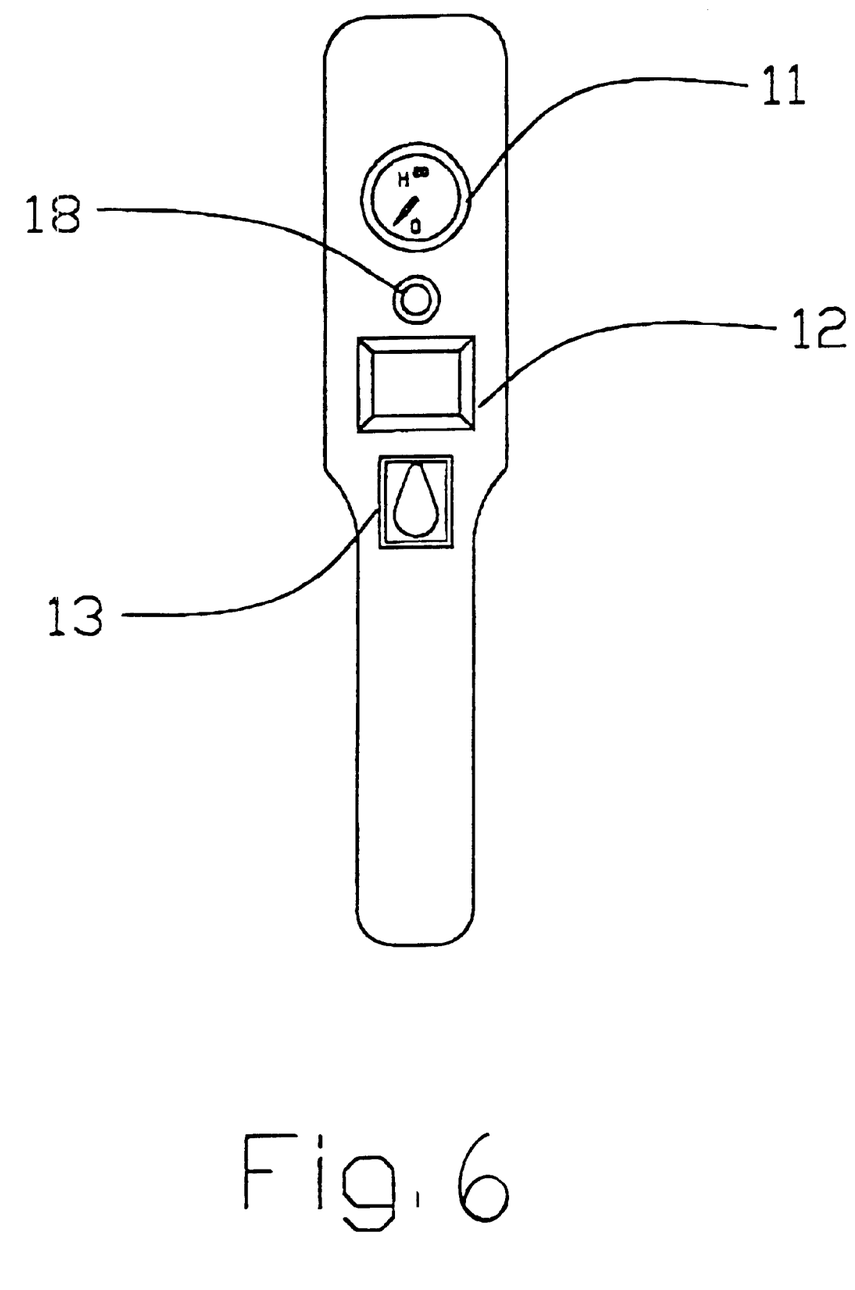
FIG. 6 is a top view of the non-invasive withdrawal and monitoring system.

Logic chips 15 are well known in the art and provide all of the processing required to convert electrical signals generated by sensing transducer 8 into a quantitative glucose concentration determination suitable for display to display 12. It should be appreciated that the logic functions performed by logic chips 15 can be equally provided by a microprocessor or computer executing analysis programs thereon, which may also include an analog-to-digital converter for converting analog signals generated by sensing transducer 8 into a digital format suitable for input to the computer. Other adaptable circuitry, including analog and digital circuitry, capable of providing the requisite analysis and display driving capabilities may suffice as a substitute for logic chips 15.

Further, logic chips or analysis circuits 15 may be provided external to housing 16, e.g., at a remote location coupled to the output of sensing transducer 8.

The display 12 may take the form of a light emitting diode (LED), liquid crystal display (LCD), or any other suitable display, including analog displays, as is well known in the art.

Once the substance measurement of interest has been determined and displayed to display 12, vacuum pump 10 and ultrasonic transducer 17 are de-energized using switch 18. Fluid displacement mechanism 1 is removed from housing 16 and replaced by a fresh, sterilized fluid displacement mechanism 1. After this, the apparatus is available for another non-invasive withdrawal of fluid from the user's skin and the associated testing of that fluid for a given constituent therein.

Figure 7:
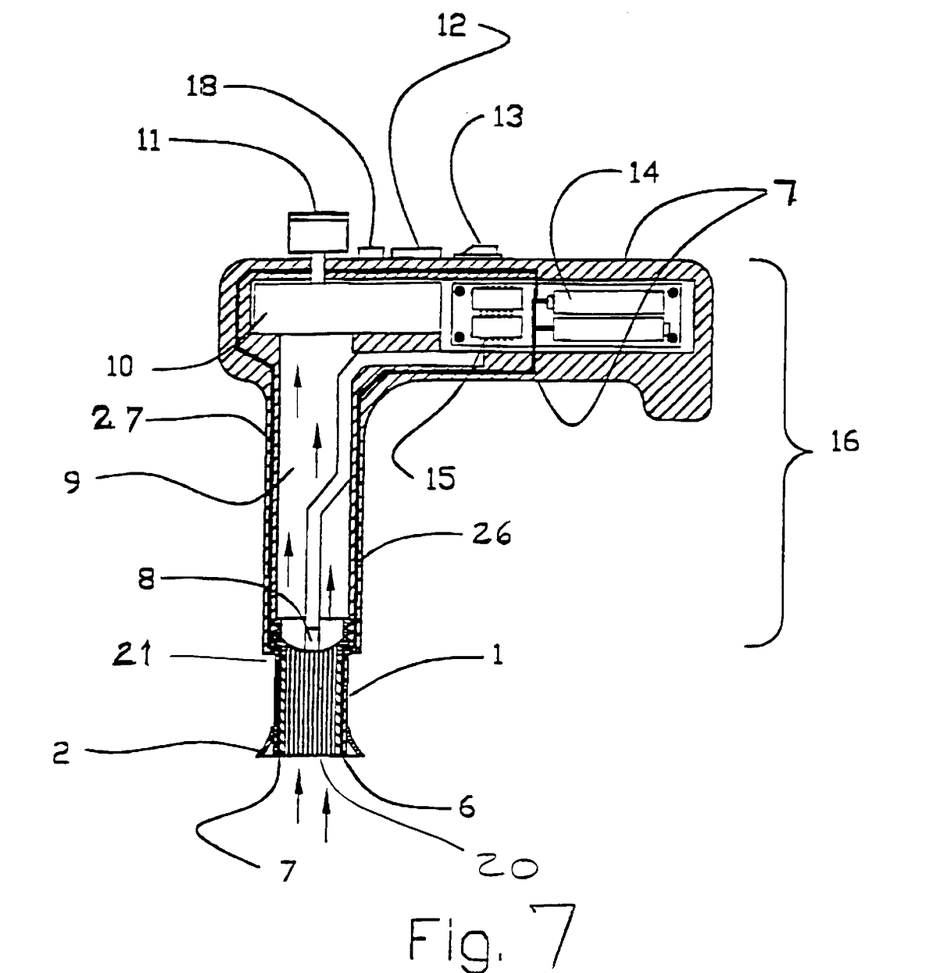
FIG. 7 is an elevational cross-sectional view of a second embodiment of the apparatus of the subject invention.
Figure 8:
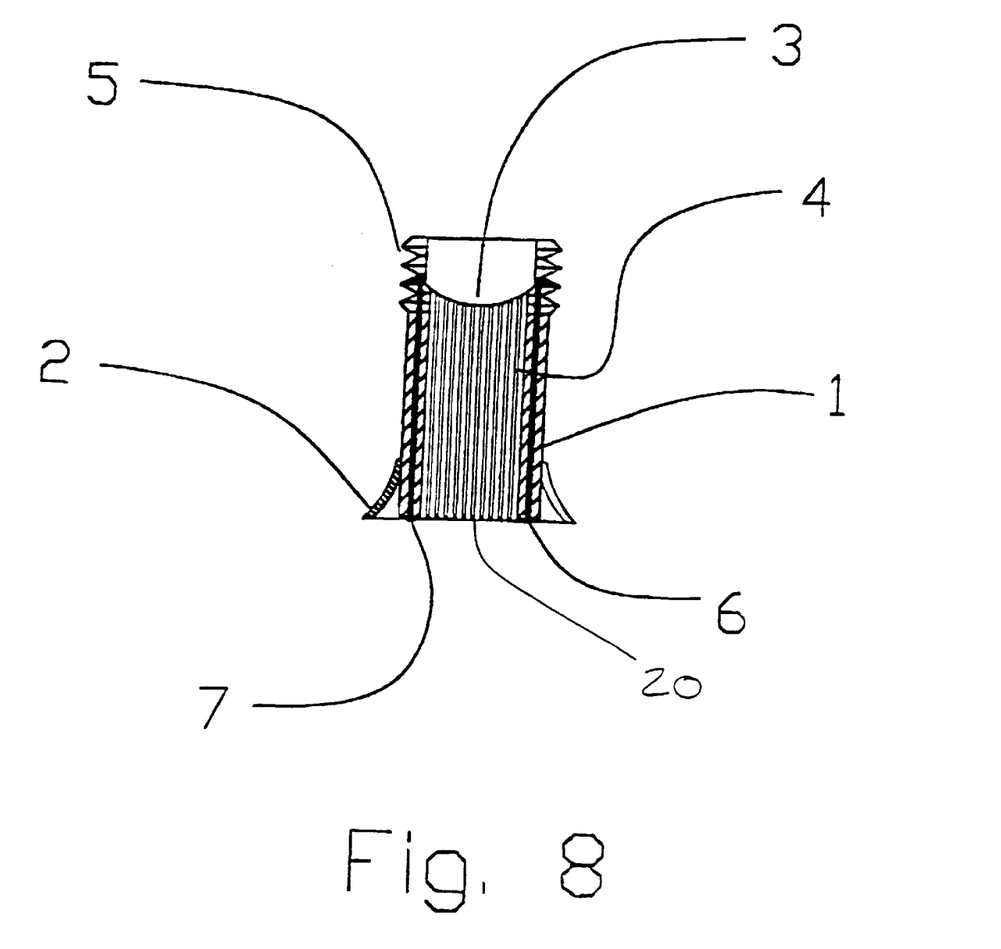
FIG. 8 is an elevational cross-sectional view of the fluid displacement mechanism shown in FIG. 7; and, FIG. 9 is an elevational cross-sectional view of a third embodiment of the apparatus of the subject invention.

In the second embodiment of the present invention, a predetermined combination of negative pressure and electric current (iontophoresis) are applied to the user's skin to non-invasively withdraw fluid therefrom. Referring to FIG. 7, the apparatus used to perform this non-invasive iontophoretic fluid extraction is similar to that provided in the first embodiment of the present invention, however, in the second embodiment, the ultrasonic transducer 17 of FIG. 1 is essentially replaced by a pair of bipolar tactile electrodes 26,27, as shown in FIGS. 7 and 8.

The positive or anode terminal of bipolar electrical power source 14 (the batteries) is electrically coupled, through insulated anode wire 6, to anodic tactile electrode 26 disposed within a wall of fluid displacement means 1. Additionally, the negative or cathode terminal of bipolar power source 14 is electrically coupled, through insulated cathode wire 7, to cathodic tactile electrode 27 also disposed within a wall of fluid displacement mechanism 1. Switch 18, which may be a simple two-pole on/off switch, in this embodiment operates to make or break electrical continuity between the power source 14 and either of the tactile electrodes 26,27 in addition to selectively activating and deactivating vacuum pump 10.

Anodic tactile electrode 26 and cathodic tactile electrode 27 form a pair of oppositely charged tactile electrodes. They are disposed in spaced relation each to the other within fluid displacement means 1, and in such a manner so as to be in direct contact with the user's skin when the user's skin is placed into contiguously interfacing contact with first end 20 of fluid displacement mechanism 1. Additionally, insulated cathode wire 7 and insulated anode wire 6 are arranged within housing 16 so as to come into electrical contact with tactile electrodes 26,27 when fluid displacement mechanism 1 is properly coupled to housing 16.

To non-invasively withdraw and monitor fluids from the user's skin in the second embodiment of the present invention, fluid displacement mechanism 1 is coupled to housing 16 in similar manner with the first embodiment described previously, thus bringing tactile electrodes 26,27 into electrical contact with insulated anode and cathode wires 6,7. After appropriately coupling fluid displacement mechanism 1 to housing 16, switch 18 is positioned to energize vacuum pump 10 and to provide electrical connectivity between the anode and cathode of power source 14, and anodic and cathodic tactile electrode 26 and 27, respectively. The first end 20 of fluid displacement mechanism 1 is pressed against the user's skin, thus applying to the contiguously interfacing area of skin the negative pressure generated by vacuum pump 10 within internal chamber 9. Further, anodic tactile electrode 26 and cathodic tactile electrode 27, now contacting the user's skin, generate an electric field therein which correspondingly induces relatively small currents, on the order of microamperes in the skin.

This combination of iontophoretically induced skin current and negative pressure applied to the skin facilitates the speedy extraction of fluid from the cellular and/or extracellular fluid of the epidermis toward the capillary conduits 4. As described previously in relation to the first embodiment of the subject invention, the non-invasively extracted fluid is emptied by capillary conduits 4 into the fluid collecting reservoir 3 for contact therein with sensing transducer 8. Sensing transducer 8 and logic circuitry 15 cooperate to provide a determination of a quantitative characteristic of a constituent of the extracted bodily fluid, as for example, the concentration of glucose therein. Measurement results are ultimately displayed to the user using display 12.

Figure 9:
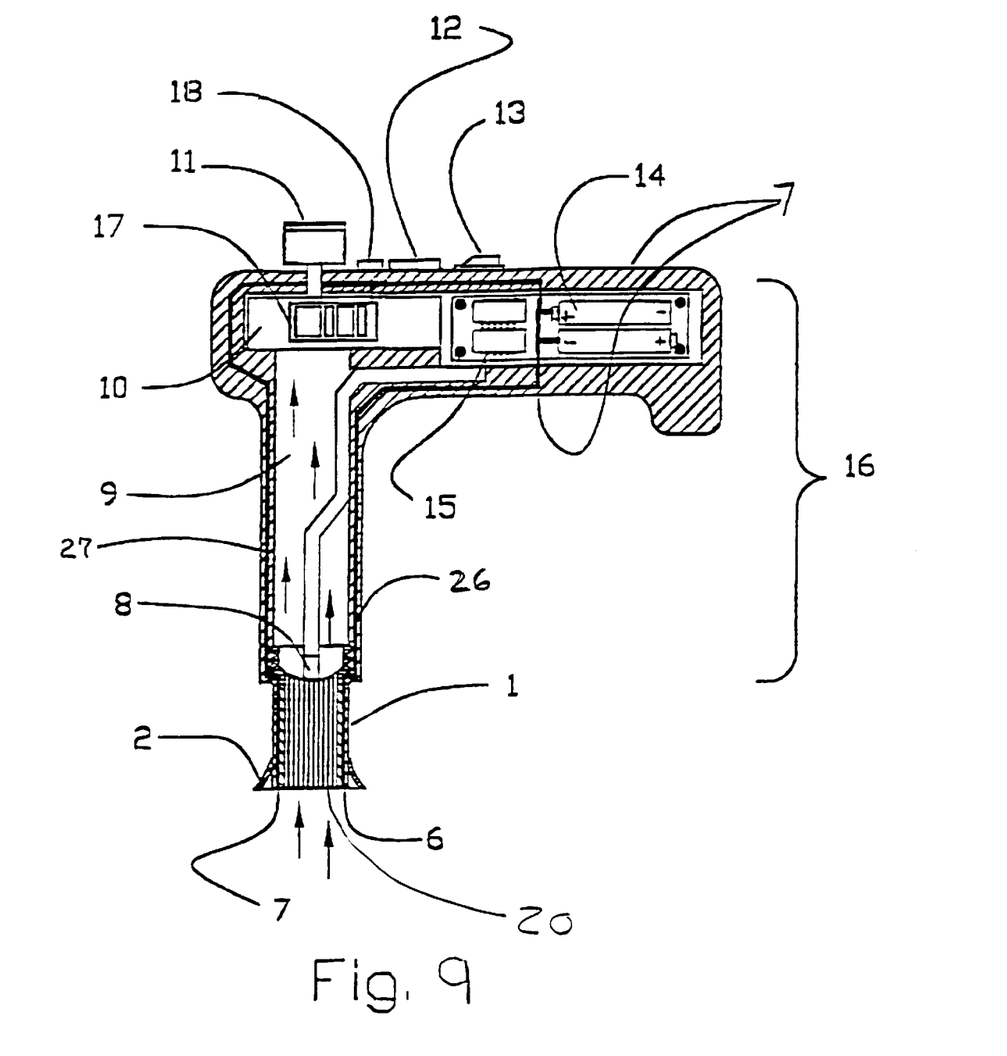

The third embodiment of the subject invention essentially combines the first two embodiments of the subject invention. Namely, a predetermined combination of negative pressure, ultrasonic energy (sonophoresis), and electric fields or electric current (iontophoresis), is applied to the user's skin to non-invasively withdraw fluids therefrom for subsequent monitoring thereof. Referring to FIG. 9, all of the elements of the apparatus described previously in relation to the first and second embodiments of the subject invention are present. In particular, the hand-held apparatus combines the vacuum pump 10 in electrical coupling to ultrasonic transducer 17 as shown in the first embodiment discussed. Electric field generation is provided by tactile electrodes 26,27 as in the second embodiment of the subject invention discussed. Switch 18 selectively energizes or activates and deactivates the vacuum pump 10, the tactile electrodes 26,27, and electronic transducer 17. However, it should be appreciated that it is well within the ordinary skill in the art to provide switch 18 with the further capability to energize the operable elements either altogether, that is, in unison, in mutual exclusion, each to the other, or in selective combination (e.g., two at a time). Such a multi-function, or multi-position switch may provide further flexibility in the use of the apparatus.

The method of non-invasively withdrawing and monitoring fluids in the embodiment of the subject invention is substantially similar to that described in relation to the first two embodiments. Fluid displacement mechanism 1 is placed into contact with the user's skin and then the vacuum pump, ultrasonic transducer, and electric field generating mechanism are energized in unison to thus apply predetermined negative pressure, ultrasonic energy and an electric field to the user's skin. This respective combination of negative pressure, iontophoresis and sonophoresis facilitates the speedy withdrawal of fluid from the user's skin, which fluid is monitored as described previously.

The subject invention concept includes a non-invasive method for withdrawing and monitoring fluid from the skin surface of a user. Initially, a housing 16 is provided being portable in nature and adapted to be hand gripped by a user. Housing 16 may be formed of a plastic composition, metal or some light material not important to the inventive concept as herein described with the exception that it be of sufficient structural rigidity to accept the loads imparted thereto.

Housing 16 includes internal chamber 9 for acceptance and fluid flow of the bodily fluids egressing from the skin of the user. Housing 16 as previously described is contiguously applied to the skin of the user to provide a substantial sealing engagement therewith.

Subsequent to the location and positioning of housing 16 on the skin of the user, fluid is non-invasively withdrawn from the skin into internal chamber 9 of housing 16. Finally, fluid entering chamber 9 is directed to sensing transducer 8 and is monitored by associative electronic mechanisms previously described within housing 16.

An important step of the subject invention concept is the non-invasive withdrawing of the fluid from the skin and such step further includes the step of applying a predetermined combined negative pressure and ultrasonic energy to the skin of the user in one form of the invention. In a second form of the invention, only a negative pressure is applied to the skin through actuation of vacuum pump 10.

In another form or embodiment of the invention, the step of non-invasive withdrawing of fluid from the skin includes the step of applying a predetermined combined negative pressure by actuation of vacuum pump 10 in combination with an electrical field applied to the skin of the user through electrodes 6 and 7. As has been discussed in previous paragraphs when describing the system of the subject invention, a further embodiment of the invention includes the step of applying a predetermined combined negative pressure through actuation of vacuum pump 10, with ultrasonic energy applied through ultrasonic transducer 17 and further in combination with the electrical field applied to the skin by electrodes 6 and 7.

The monitoring of the fluid is accomplished by sensing a constituent of the fluid and analyzing the constituent sensed in the fluid to determine some quantitative characteristic thereof.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A non-invasive system for withdrawing and monitoring a fluid drawn through a user's skin comprising:

(a) a housing having an internal chamber;

(b) fluid displacement means for directing said fluid from the user's skin into said internal chamber, said fluid displacement means having a first end positionally located contiguous an outer surface of the user's skin and an opposing second end disposed internal said housing;

(c) vacuum generating means in open communication with said internal chamber for generating a negative pressure of a predetermined magnitude therein;

(d) energy generating means disposed within said housing and coupled to said internal chamber for generating energy at a level not greater than that which reduces cohesiveness of cells of a stratum cornium layer of the user's skin, said negative pressure in said internal chamber and said generated energy being transmitted through said fluid displacement means to the user's skin; and, (e) monitoring means within said internal chamber of said housing for monitoring said fluid drawn into said internal chamber.

2. The system as recited in claim 1 where said energy generating means includes an ultrasonic transducer coupled to said internal chamber for generating ultrasonic energy.

3. The system as recited in claim 1 where said energy generating means includes electric field generating means in contiguous contact with the user's skin for inducing a current therein.

4. The system as recited in claim 2 where said energy generating means further includes electric field generating means in contiguous contact with the user's skin for inducing a current therein.

5. A non-invasive system for withdrawing and monitoring a fluid drawn through a user's skin comprising:
   (a) a housing having an internal chamber;
   (b) fluid displacement means for directing said fluid from the user's skin into said internal chamber, said fluid displacement means having a first end positionally located contiguous an outer surface of the user's skin and an opposing second end disposed internal said housing, said fluid displacement means including a tubular structure coupled to said housing, said tubular structure having a plurality of capillary conduits extending between said first and second ends;
   (c) means for non-invasively extracting said fluid from the user's skin and for drawing said extracted fluid into said internal chamber through said fluid displacement means, said means for non-invasively extracting said fluid being positioned within said housing; and,
   (d) monitoring means within said internal chamber of said housing for monitoring said fluid drawn into said internal chamber.

6. A non-invasive system for withdrawing and monitoring a fluid drawn through a user's skin comprising:
   (a) a housing having an internal chamber;
   (b) fluid displacement means for directing said fluid from the user's skin into said internal chamber, said fluid displacement means having a first end positionally located contiguous an outer surface of the user's skin and an opposing second end disposed internal said housing, said fluid displacement means including a tubular structure coupled to said housing, said tubular structure having a plurality of capillary conduits extending between said first and second ends; said fluid displacement means including a sealing member mounted to a peripheral edge of said first end of said fluid displacement means, said sealing member forming a substantially air-tight seal between said sealing member and the user's skin in contact therewith;
   (c) means for non-invasively extracting said fluid from the user's skin and for drawing said extracted fluid into said internal chamber through said fluid displacement means, said means for non-invasively extracting said fluid being positioned within said housing; and,
   (d) monitoring means within said internal chamber of said housing for monitoring said fluid drawn into said internal chamber.

7. A non-invasive method for withdrawing and monitoring a fluid drawn through a user's skin, including the steps of:
   (a) providing a housing having an internal chamber, said housing being contiguously applied to a selected portion of the user's skin;
   (b) applying a negative pressure to the selected portion of the user's skin;
   (c) applying energy to the selected portion of the user's skin substantially simultaneous with said application of said negative pressure to draw fluid into said internal chamber, said energy being applied at a level not greater than that which reduces cohesiveness of cells of a stratum cornium layer of the user's skin; and,
   (d) monitoring said fluid to determine at least one predetermined characteristic thereof.

8. The method as recited in claim 7 where the step of applying energy includes the step of applying ultrasonic energy to the selected portion of the user's skin.

9. The method as recited in claim 7 where the step of applying energy includes the step of applying an electric field to the selected portion of the user's skin.

10. The method as recited in claim 7 where the step of applying energy includes the step of applying ultrasonic energy, and an electric field to the selected portion of the skin.

* * * * *